US010238439B2

(12) United States Patent
Prybis et al.

(10) Patent No.: US 10,238,439 B2
(45) Date of Patent: Mar. 26, 2019

(54) ANTERIOR SPINAL BONE PLATE HOLDING SYSTEM AND METHOD

(71) Applicant: Meditech Spine, LLC, Atlanta, GA (US)

(72) Inventors: Brad G. Prybis, Mableton, GA (US); Robert Bruce Dunaway, Akron, OH (US); Amanda Shade, Fairview Park, OH (US); Eric Flickinger, Atlanta, GA (US)

(73) Assignee: MEDITECH SPINE, LLC, Atlanta, GA (US)

( * ) Notice: Subject to any disclaimer, the term of this patent is extended or adjusted under 35 U.S.C. 154(b) by 140 days.

(21) Appl. No.: 15/136,660

(22) Filed: Apr. 22, 2016

(65) Prior Publication Data

US 2016/0310180 A1 Oct. 27, 2016

Related U.S. Application Data

(60) Provisional application No. 62/152,545, filed on Apr. 24, 2015.

(51) Int. Cl.
*A61B 17/80* (2006.01)
*A61B 17/00* (2006.01)

(52) U.S. Cl.
CPC .......... *A61B 17/808* (2013.01); *A61B 17/80* (2013.01); *A61B 2017/00433* (2013.01); *A61B 2017/00858* (2013.01); *A61B 2017/00867* (2013.01); *A61B 2017/00955* (2013.01)

(58) Field of Classification Search
CPC .......... A61B 17/808; B25B 9/00; B25B 27/02
See application file for complete search history.

(56) References Cited

U.S. PATENT DOCUMENTS

| 3,540,322 | A | * | 11/1970 | Swanson | ................. B23B 49/02 408/112 |
| 3,574,381 | A | * | 4/1971 | Ocheltree | ................. B25B 9/00 294/94 |
| 5,423,826 | A | * | 6/1995 | Coates | ............... A61B 17/1728 606/281 |
| 5,683,399 | A | * | 11/1997 | Jones | ........................ A61F 2/34 606/91 |
| 5,851,207 | A | * | 12/1998 | Cesarone | ........... A61B 17/1728 606/86 B |
| 6,342,057 | B1 | * | 1/2002 | Brace | ................. A61B 17/1728 606/96 |

(Continued)

*Primary Examiner* — David W Bates
(74) *Attorney, Agent, or Firm* — Kilpatrick Townsend & Stockton LLP

(57) ABSTRACT

A bone plate holder apparatus having a hollow shaft, two or more prongs at a working end, and a rod slidingly disposed within the shaft can be attached with a bone plate such that the prongs interact with a fenestration in the bone plate. When the rod is depressed between the prongs, working surfaces of the prongs grip the interior surfaces of the fenestration, causing the bone plate holder apparatus to lock to the bone plate. Bone plate holder systems including a bone plate holder apparatus and bone plate can be used to install a bone plate in a surgical site in a patient, and the locking and unlocking functionality of the bone plate holder apparatus can permit adjustment of an angle of the bone plate holder apparatus relative to the bone plate with ease during surgery.

20 Claims, 8 Drawing Sheets

(56) References Cited

U.S. PATENT DOCUMENTS

| | | | | |
|---|---|---|---|---|
| 6,692,503 | B2* | 2/2004 | Foley | A61B 17/1728 |
| | | | | 606/282 |
| 8,303,601 | B2* | 11/2012 | Bandeira | A61B 17/025 |
| | | | | 606/90 |
| 9,750,512 | B2* | 9/2017 | Jerke | A61B 17/1728 |
| 2003/0083667 | A1* | 5/2003 | Ralph | A61B 17/1728 |
| | | | | 606/96 |
| 2004/0015174 | A1* | 1/2004 | Null | A61B 17/1728 |
| | | | | 606/99 |
| 2005/0015092 | A1* | 1/2005 | Rathbun | A61B 17/1728 |
| | | | | 606/96 |
| 2005/0038444 | A1* | 2/2005 | Binder, Jr. | A61B 17/1728 |
| | | | | 606/96 |
| 2005/0228400 | A1* | 10/2005 | Chao | A61B 17/7082 |
| | | | | 606/104 |
| 2007/0093897 | A1* | 4/2007 | Gerbec | A61F 2/4465 |
| | | | | 623/17.11 |
| 2011/0106169 | A1* | 5/2011 | Zalenski | A61B 17/7071 |
| | | | | 606/279 |
| 2014/0243829 | A1* | 8/2014 | Cavallazzi | A61B 17/74 |
| | | | | 606/71 |

* cited by examiner

ANTERIOR SPINAL BONE PLATE HOLDING SYSTEM AND METHOD

CROSS-REFERENCE TO RELATED APPLICATION

This application claims priority to U.S. Provisional Application Ser. No. 62/152,545 filed Apr. 24, 2015 and titled "Anterior Spinal Bone Plate Holding System and Method," the entire contents of which are hereby incorporated by reference.

BACKGROUND

Broken bones heal naturally, albeit slowly, compared to most soft tissue, provided they are adequately supported and relieved of stress. In a simple break in an extremity, adequate support and relief may be provided from outside the body with a device as simple as a splint or a cast, which immobilizes the body part containing the broken bone. Such procedures may suffice when the bone can be set and will retain its position without significant intervention, for instance when the break is simple and contained in a body part that can be readily immobilized in a natural posture. Immobilization is also therapeutic to treat damage to connective tissue by preventing repetitive stress and further injury to, for instance, damaged ligaments, tendons, or cartilage. Degenerative conditions may also be treated with immobilization, and particularly degenerative conditions of the spine. For example, spinal degenerative conditions may include slipped, herniated or ruptured discs, spinal stenosis, osteoarthritis, degenerative disc disease and other conditions. Misaligned vertebrae, or vertebrae repositioned in the course of reconstructive surgery, may also be immobilized permanently or temporarily to support the spine during healing or spinal fusion.

When a break, fracture, degenerative condition, or misalignment affects the spine, or when the connective tissue between one or more vertebrae is damaged, external immobilization is significantly less effective for several reasons. Because the spine is the central support column of the human body, externally imposed immobilization is impractical, as it implies immobilizing most of the body. Furthermore, the spine is aloud-hearing structure that is subject to repetitive compressive and rotational stresses constantly during the normal waking life of a person; therefore, external immobilization of the spine significantly impacts the mobility and activity of a patient. For practical purposes, externally imposed spinal immobilization often requires that the patient is subjected to bed rest, is wheelchair-bound, is fitted with a significant amount of uncomfortable stabilizing equipment, or a combination of the above.

Since the advent of sterile surgery, it has been possible for doctors to internally stabilize broken bones and connective tissue with implants. Internal stabilization can be complex, but tends to allow much greater precision in aligning broken bones, and significantly reduces misalignment in healing. Internal stabilization also improves healing time and allows a patient to live a much more normal life while still healing. One such type of implant is a bone plate, which is a shaped rigid or semirigid part usually having several through-holes by which a surgeon will attach the plate to parts of a broken bone, or to parts of two or more proximate bones that require alignment, using screws.

Various aspects of the surgical procedure of installing a bone plate impact patient outcomes. For example, the bone plate must be properly aligned with the underlying bone, and retained in alignment during attachment. Also, the duration of an installation procedure, and the tissue displacement required for the procedure, should be minimized as much as practicable to minimize trauma. The tools and methods for inserting and stabilizing a bone plate for surgical insertion and revision very much impact these aspects of the surgical procedure.

BRIEF SUMMARY

The following presents a simplified summary of some embodiments to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Disclosed is a bone plate holder apparatus, which can include a substantially elongate shaft having a working end and a handle end and at least two opposed prongs at the working end, the prongs converging towards a longitudinal axis of the hollow shaft. The bone plate holder apparatus can include an elongate rod disposed substantially parallel to and/or within the hollow shaft, the rod being sized to interfere with the prongs at a first end of the rod and press the prongs outward when the rod is pressed toward the working end of the hollow shaft. The bone plate holder apparatus can also include a cam having an axis of rotation generally perpendicular to a longitudinal axis of the hollow shaft and proximate to the handle end, the cam being positioned to abut a second end of the rod, and having a variable radius such that the cam can alternatingly press and release the rod between a "locked" and an "unlocked" position, respectively. The bone plate holder apparatus can also include a handle attached with the cam, the handle being configured to cause the cam to rotate between a first position and a second position, the first position being associated with the unlocked position and the second position being associated with the locked position.

Also disclosed are bone plate holder systems that include a bone plate holder apparatus, such as described above, and a bone plate. The bone plate can have an interior fenestration sized to accommodate the at least two opposed prongs of the bone plate holder apparatus, such that the opposed prongs interfere with the fenestration when the prongs are pressed outward.

Also disclosed are methods of installing a bone plate in a surgical site of a patient using a bone plate holder apparatus. Exemplary methods include attaching a bone plate holder apparatus with a bone plate in an unlocked position, adjusting an angle between the bone plate holder apparatus and the bone plate to a first angle and locking the bone plate holder apparatus to retain the bone plate at the first angle or a second angle. A physician using the bone plate holder apparatus can unlock the bone plate holder apparatus, adjust the first or second angle, and lock the apparatus again as needed. In this way, a physician can conveniently adjust and secure the angle between the bone plate holder apparatus and the bone plate before and during surgery to access attachment means of the bone plate at the surgical site. In some examples, a plate holder apparatus attached with a bone plate may have one or more degrees of lateral freedom, or partial freedom, such that a physician may conveniently adjust and secure the point of attachment on the bone plate before and/or during surgery.

For a fuller understanding of the nature and advantages of the present invention, reference should be made to the ensuing detailed description and accompanying drawings.

BRIEF DESCRIPTION OF THE DRAWINGS

These and other features, embodiments, and advantages of the present disclosure are better understood when the following Detailed Description is read with reference to the accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Disclosed are apparatuses, systems and methods for holding a bone plate for insertion or revision surgery. In one example, a plate holder apparatus has a hollow elongate shaft terminating at a working end, with an opening and at least two prongs at the working end, the prongs being bent toward a center longitudinal axis of the shaft and each prong having a working surface facing away from a center longitudinal axis of the hollow shaft. In some cases, prongs can be offset from the center of the hollow shaft, i.e. toward an offset longitudinal axis. The hollow elongate shaft may accommodate a rod therethrough, the rod configured to press the prongs apart when the rod is depressed. At a handle end of the elongate shaft, a cam may be positioned within a portion of the shaft and attached with a rotating lever, so that a working surface of the cam can alternatingly depress or release the rod. In a depressed state, the rod end interferes with the bent portion of the prongs, forcing the prongs apart, such that the prong working surfaces can be pressed outward against a surrounding fenestration in a bone plate to hold it in a "locked" position. In a released state, or "unlocked" position, the rod does not interfere with the prongs, so that the working surfaces of the prongs are free to be inserted into or removed from a surrounding fenestration, or adjusted in angle relative to the bone plate.

Figure 1:
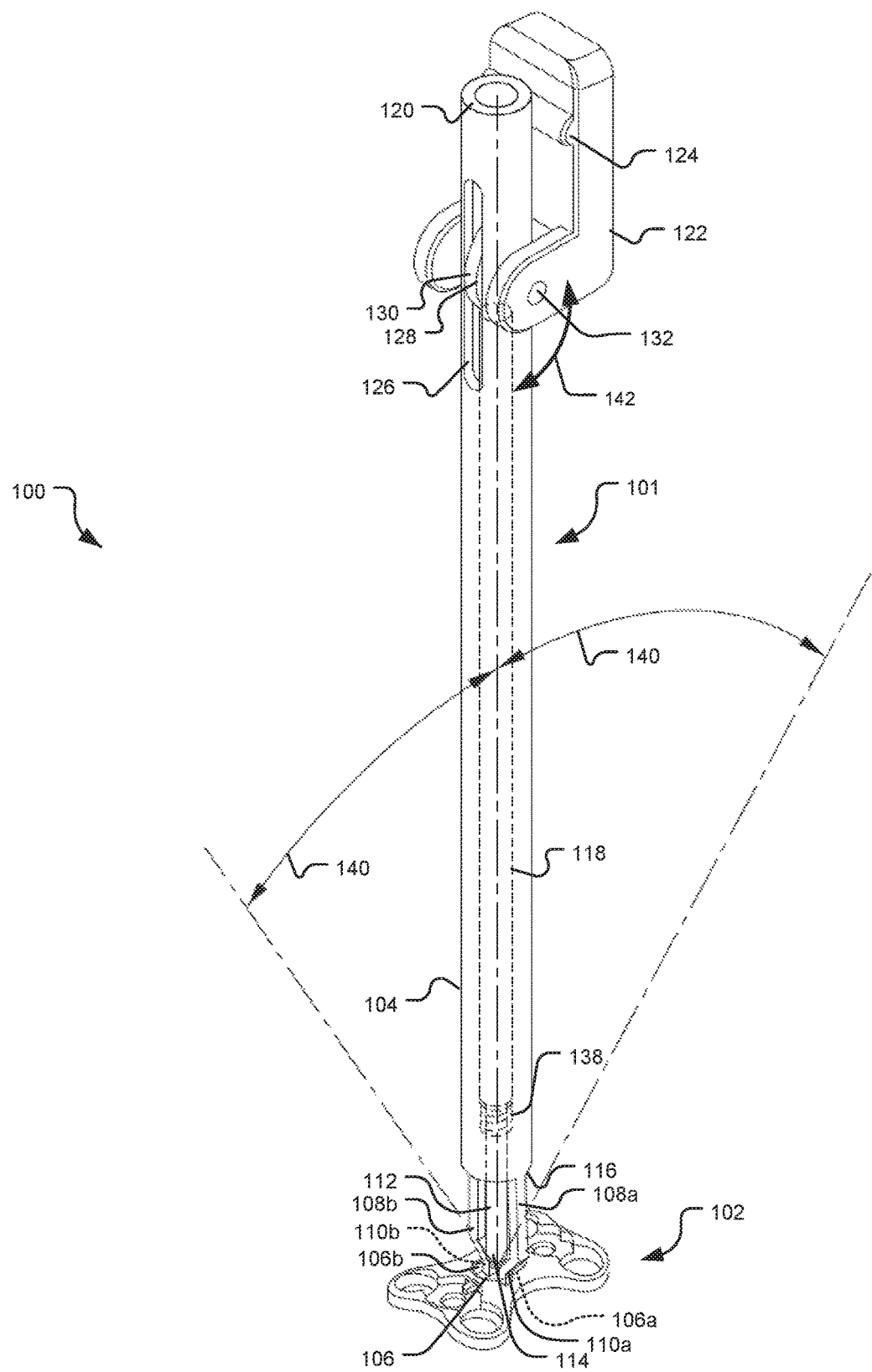
FIG. 1 is a perspective view of a bone plate holder system according to one example.

Referring now to the drawings, in which like reference numerals represent like parts throughout the several views, FIG. 1 shows a bone plate holder system 100 including a bone plate holder apparatus 101 and a bone plate 102. The bone plate 102 includes an interior fenestration 106 having opposed interior faces 106a and 106b. The bone plate holder apparatus 101 includes a hollow elongate shaft 104 terminating at a working end 116 having prongs 108a, 108b extending away from the working end 116 and converging toward an interior axis of the elongate shaft 104. A rod 112 runs substantially parallel with the elongate shaft 104. In the illustrated example, the rod 112 is coaxially received inside an interior lumen 118 of the hollow shaft 104. The rod 112 is configured to press against the prongs 108a, 108b at a rod end 114 of the rod 112. The prongs 108a, 108b have prong working surfaces 110a, 110b that face away from the interior axis of the shaft 104 and that are configured to interact with the opposed interior faces 106a, 106b of the interior fenestration 106 of the bone plate 102. The bone plate holder system 100 is shown in FIG. 1 in a "locked" position, where the rod 112 and particularly the rod end 114 is pressed in-between the prongs 108a, 108b, separating the prongs 108a, 108b and causing the prong working surfaces 110a, 110b to forcibly abut the opposed interior faces 106a, 106b, causing the bone plate holder apparatus 101 to substantially "lock" to and become mechanically attached with the bone plate 102.

A bone plate holder system may include a bone plate with an interior fenestration that is shallower in depth than the working surfaces of the prongs of a bone plate holder apparatus. In such cases, the prongs of the bone plate holder apparatus may extend below an inferior surface of the bone plate, and may include positive, grip enhancing surface features extending outward from the tips of the working surfaces of the prongs for gripping an inferior surface of the bone plate. Alternatively, the prong working surfaces may have grooves (or other such features) sized to match the thickness of the bone plate at the interior fenestration, so that the prongs grip the bone plate at the inferior and superior surfaces as well as at the opposed interior faces of the fenestration. Or, alternatively, the prong working surfaces may have positive surface features only disposed at a distance from the tips of the prongs, the distance approximately matching the depth of the fenestration, such that the prongs of a bone plate holder apparatus are prevented from extending beyond that depth into the fenestration in the bone plate, for example, to protect underlying tissue from inadvertent slippage of the bone plate holder apparatus.

A bone plate may alternatively have a substantially elongate fenestration having at least two parallel interior faces, configured for permitting a bone plate holder apparatus to connect with the bone plate at more than one location along the elongate fenestration. The parallel interior faces of an elongate fenestration may be smooth or configured to allow prongs in a bone plate holder apparatus, such as the apparatus 101 shown in FIG. 1, to slide along the fenestration. The parallel interior faces of an elongate fenestration may alternatively have surface features, such as grooves or positive surface features, configured for guiding the prongs of a bone plate holder apparatus to two or more positions or orientations, or to interact with the prongs to provide tactile feedback to a practitioner and/or to enhance the locking or gripping power of the prongs at those positions or orientations. In some alternatives, more than one fenestration may be present in a bone plate.

The bone plate holder apparatus 101 has a handle 122 attached with the hollow shaft 104 proximate to a handle end 120. The handle 122 is coupled with a cam 128 having a cam working surface 130 configured to abut and interact with the rod 112. The cam 128 is rotatably attached within a cavity 126 in the hollow shaft 104 by an axle 132, and the handle 122 is attached with the axle 132, so that manipulating the handle 122 causes the cam 128 to rotate. As shown in FIG. 1, the cam 128 causes the rod 112 to press in-between the prongs 108a, 108b, as described above.

Bone plate holder apparatus 101 may include one or more surface features on the handle 122, such as a positive surface feature 124, for controlling a range of angles 142 of the handle 122. The range of angles 142 of the handle 122 may be controlled to cause the handle to "lock" into the locked position, for example by causing the cam 128 to rotate through and past a widest point, such that a force on the handle 122 in an unlocking direction must be exerted to release the handle 122 from the "locked" position. The range of angles 142 may include a range of approximately 90 degrees, or more or less than 90 degrees. The shaft 104 of the bone plate holder apparatus 101 may also include one or more fenestrations in the shaft to provide access for cleaning the apparatus; knurled or textured surface features to provide a gripping surface or grip-enhancing surface that can enable a practitioner to better grip the apparatus with wet gloves; and/or may include flat or contoured sections for better ergonomics or improved hand control. Alternatively or additionally, one or more surface features within the lumen 118 of the shaft 104 of the bone plate holder apparatus 101, and on the rod 112, may be configured to stop the motion of the rod in the shaft at either or both of a minimum and maximum travel.

The cam 128 and/or the cam working surface 130 may possess one or more flat portions and curved portions, the flat portion(s) corresponding to the locked and unlocked positions and the curved portion(s) corresponding to a variable radius, such that the cam 128, and by extension the handle 122 and rod 112, may occupy stable positions when the cam 128 is oriented with a flat portion abutting the rod 112. The cam working surface 130 may alternatively or additionally possess any suitable number of intermediate flat portions, negative surface features, and/or positive surface features, which may provide tactile feedback to a user regarding the orientation of the cam 128 as a user rotates the handle 122.

In various examples, a turning mechanism other than the handle 122 may be provided for rotating the cam 128. For example, any suitable mechanism that can be gripped by a user may replace the handle 122, such as a knob or comparable device. In some alternatives, a turning mechanism may be provided which interfaces with another tool, e.g. a driver, wrench, key, or comparable device.

Prong working surfaces 110a, 110b of the prongs 108a, 108b may be configured to grip the opposed interior faces 106a, 106b of the bone plate 102. For example, the prong working surfaces 110a, 110b may be textured or include a high-friction surface feature, such as a rubber or plastic coating, or may include indentations, grooves, or any combination of positive and negative surface features for enhancing grip. The opposed interior faces 106a, 106b may also or alternatively possess any of a texture, a high-friction surface feature, indentations, grooves, or any such positive and/or negative features for enhancing grip. In addition, the surfaces may be configured to permit the prong working surfaces 110a, 110b to grip the opposed interior faces 106a, 106b when the faces are at a suitable angle with respect to one another, such as when the bone plate holder apparatus 101 is tilted at an angle 140 with respect to the bone plate 102. The angle may be any suitable angle, but in some non-limiting examples may be between +90 degrees and −90 degrees (where 0 degrees is perpendicular to the bone plate 102). In various other examples the angle may be between ±85 degrees, ±80 degrees, ±75 degrees, ±70 degrees, ±65 degrees, ±60 degrees, ±55 degrees, ±50 degrees, ±45 degrees, or any suitable angle.

One or both of the prong working surfaces 110a, 110b, and opposed interior faces 106a, 106b may be configured with grooves or other suitable features that cause the bone plate holder apparatus 101 to lock into one or more particular holding angles of a medical implant. For example, grooves may provide for holding a medical implant, e.g. a bone plate, at any combination of holding angles relative to the bone plate holder apparatus 101 including one or more of 0 degrees; ±10 degrees; ±20 degrees; ±30 degrees, ±45 degrees, ±60 degrees; or any other suitable angle.

In some examples, when the rod is in a depressed position, the prongs 108a, 108b act against the rod end 114 to cause the bone plate holder apparatus 101 to "unlock" when the rod 112 is released, i.e. when the cam 128 rotates to the unlocked position from the locked position. However, in alternative examples, a spring assembly 138 interior to the shaft 104 acts against one or more surface features (not shown) of the rod 112, pressing the rod 112 toward the released or "unlocked" position, such that the rod is retained in a released position when not depressed and such that the rod returns to a released position from the depressed position when released by the cam 128.

The bone plate holder apparatus and bone plate may be formed of any suitable biocompatible material, including but not limited to: surgical-grade stainless steel or any biocompatible metal alloy including titanium alloys, cobalt-chrome alloys, or other biocompatible metallic materials. Alternatively, the bone plate holder apparatus may be formed of high-performance plastics, such as polyether ether ketone (PEEK), or any other suitable material. Any or all of a bone plate 102 and bone plate holder apparatus 101 may also be formed of a shape-memory alloy. The bone plate 102 and any or all individual part(s) of the bone plate holder apparatus 101 may be anodized and/or color coded, for example, to readily differentiate the bone plate holder apparatus 101 from the bone plate 102, to differentiate different configurations or lengths of bone plate holder apparatus, to differentiate different sizes or configurations of plates, or to distinguish parts within a single bone plate holder apparatus. For example, a rod 112 may be provided that is a different color than the shaft 104 or prongs 108a, 108b, such that the locked or unlocked position is more readily visible.

Figure 2:
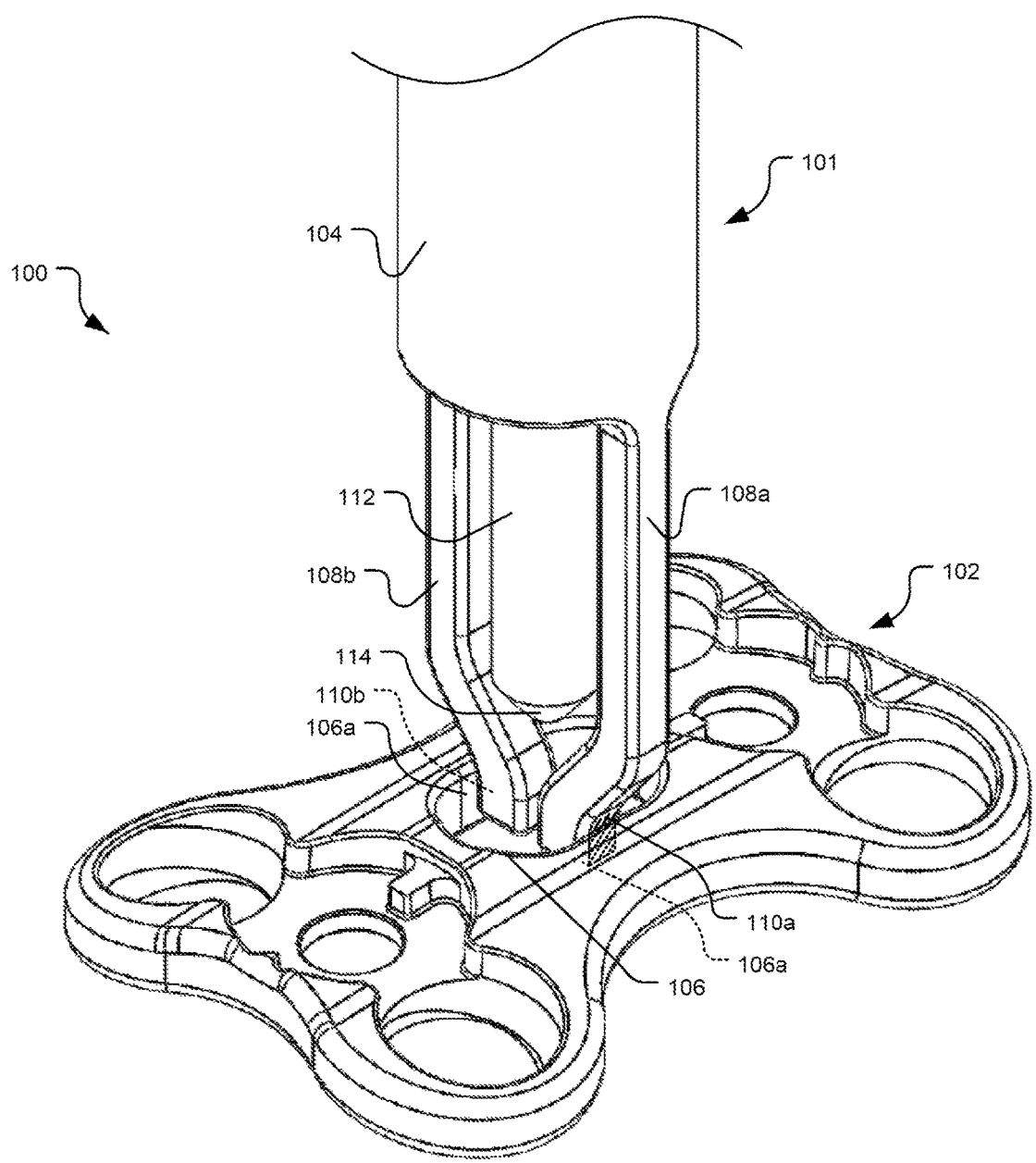
FIG. 2 is a partial perspective view of the plate holder system of FIG. 1, showing the working end of a plate holder apparatus interacting with a bone plate, in an unlocked position, and schematically showing gripping surface features of the plate holder apparatus prongs.

FIG. 2 shows the bone plate holder system 100 of FIG. 1, in a partial perspective view focused on the working end 116 of the bone plate holder apparatus 101, as it interacts with the bone plate 102, in an unlocked position. As shown, the shaft 104 is oriented approximately perpendicular to the bone plate 102, and the prongs 108a, 108b and prong working surfaces 110a, 110b are positioned within a space interior to the opposed interior faces 106a, 106b of the bone plate. The prongs 108a, 108b are in an un-flexed position, and the rod end 114 is not impinging on the prongs 108a, 108b such that the prong working surfaces 110a, 110b are not caused to exert significant force on the opposed interior faces 106a, 106b.

In some examples, the prongs 108a, 108b in an unlocked position are sufficiently narrow so that an outer width of the prong working surfaces 110a, 110b is less than a space between the opposed interior faces 106a, 106b of the bone plate 102. In other examples, the outer width of the prong working surfaces 110a, 110b is the same as or slightly larger than the space between the opposed prong working surfaces 110a, 110b, such that the "unlocked" prongs bend slightly when inserted between the opposed interior faces, but exert significantly less force than "locked" prongs. In some cases, the force exerted by the prongs 108a, 108b on the opposed interior faces 106a, 106b is sufficiently low that the bone plate holder apparatus 101 can be inserted into and removed from the bone plate 102 easily, but sufficiently high that the bone plate holder apparatus 101 can support the weight of a bone plate in the unlocked position, such that the plate can be loosely attached with the bone plate holder apparatus 101 and positioned at a desired angle relative to the holder apparatus prior to locking the plate and holder apparatus together.

Figure 3:
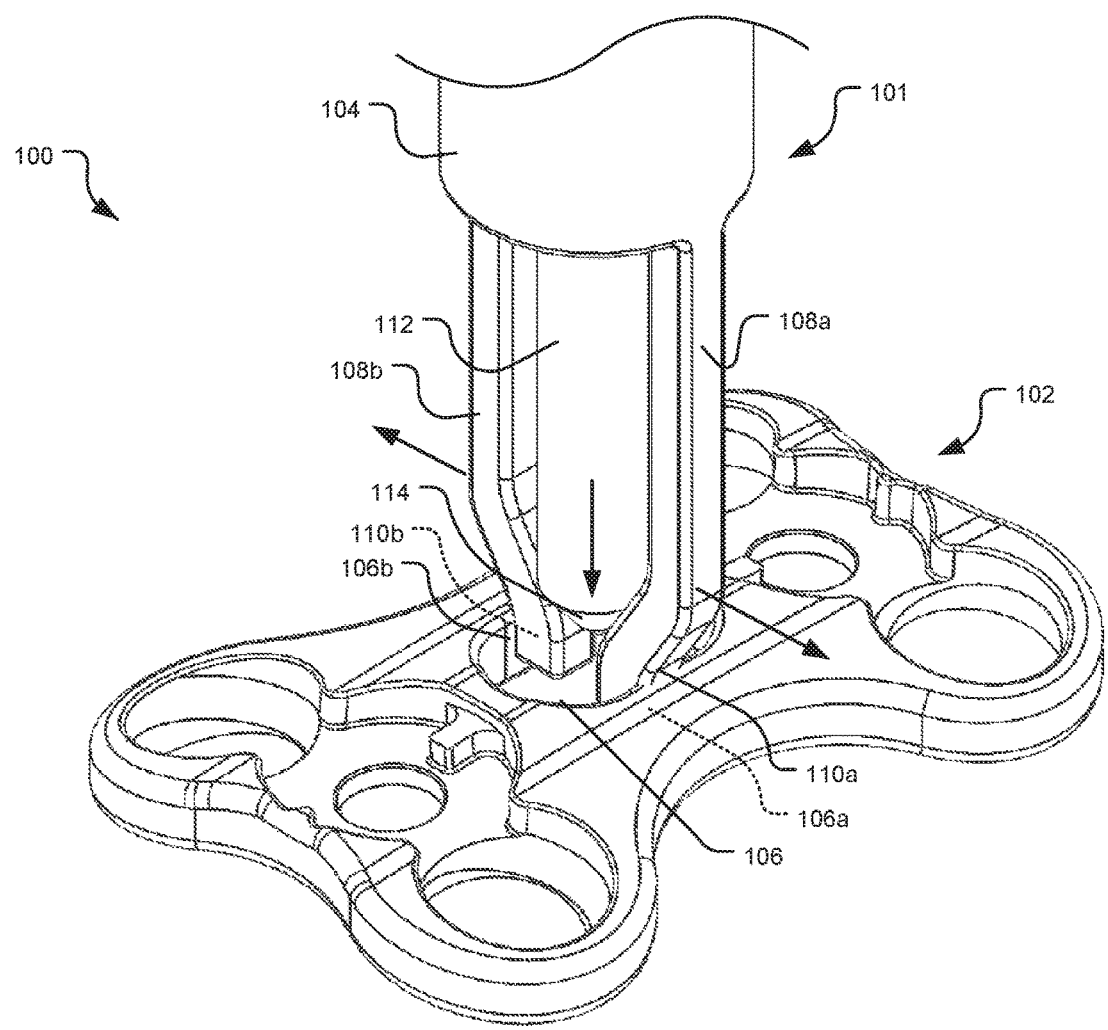
FIG. 3 is a partial perspective view of the plate holder system of FIG. 1, showing the working end of a plate holder apparatus interacting with a bone plate, in a locked position.

FIG. 3 shows the bone plate holder system 100 of FIG. 1, in a partial perspective view focused on the working end of a bone plate holder apparatus 101, interacting with the bone plate 102, in a locked position. As shown, the rod 112 is depressed toward the bone plate 102 (compared to an unlocked position, as shown in FIG. 2), causing the rod end 114 to impinge on the prongs 108a, 108b, causing them to expand outward. When the prongs 108a, 108b expand outward, the prong working surfaces 110a, 110b are driven forcibly into the interior faces 106a, 106b of the bone plate 102, causing bone plate holder apparatus 101 to mechanically lock to the bone plate 102.

Figure 4A:
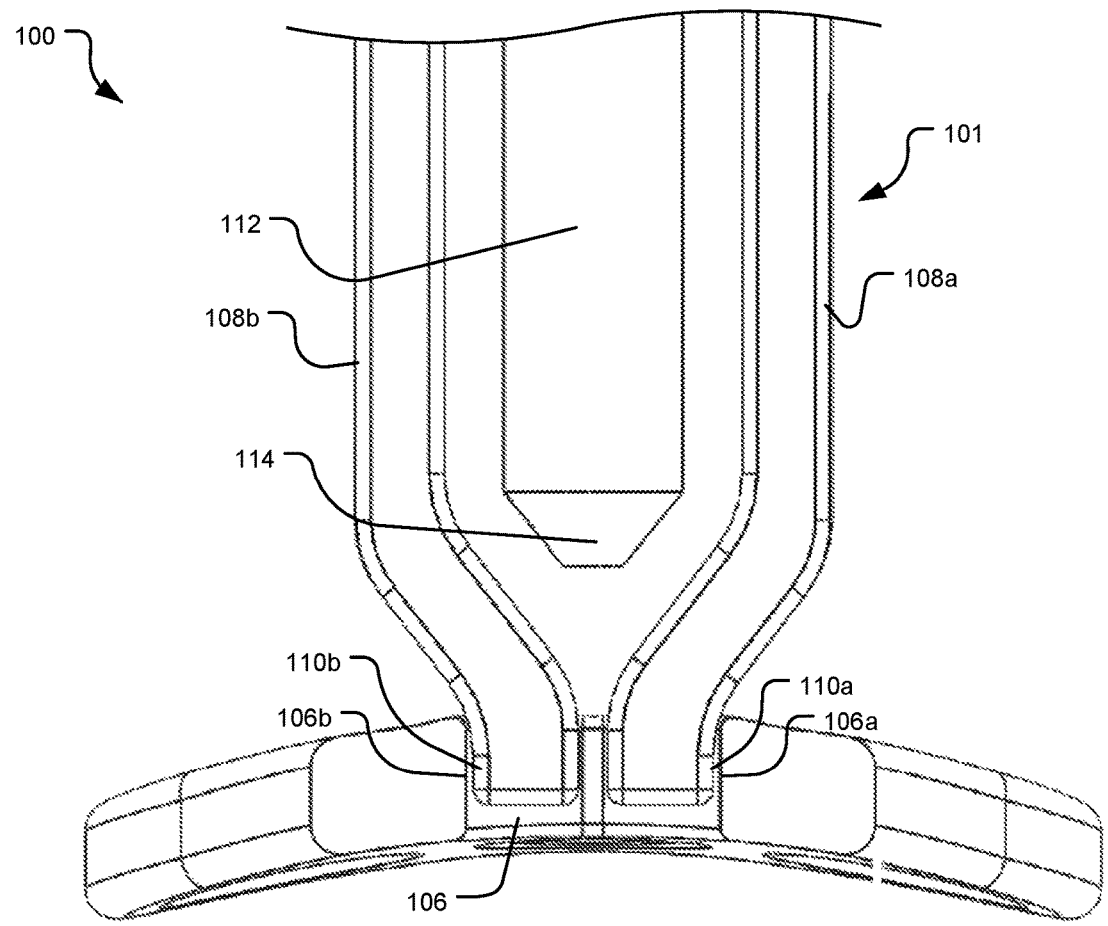
FIG. 4A is a partial side cutaway schematic view of the plate holder system of FIG. 1, showing the working end of a plate holder apparatus interacting with a bone plate in schematic view, in an unlocked position.
Figure 4B:
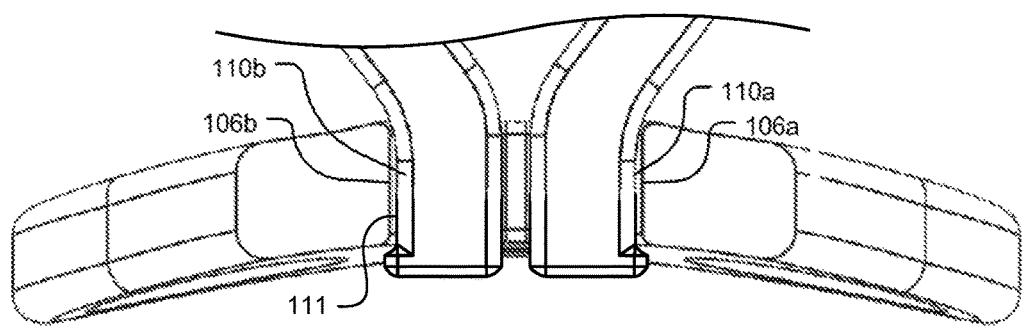
FIG. 4B is a partial side cutaway schematic view showing an alternative embodiment of the plate holder system of FIG. 1, showing the working end of a plate holder apparatus with grooved prongs.

FIG. 4A is a partial side cutaway schematic view of the bone plate holder system 100 of FIG. 1, showing the working end of the bone plate holder apparatus 101 interacting with a bone plate 102, in an unlocked position. As shown in FIG. 2, the rod 112 is in a released position, where the rod end 114 is not interacting with the prongs 108a, 108b. The prong working surfaces 110a, 110b of the prongs 108a, 108b are not in forced contact with the interior faces 106a, 106b of the bone plate 102. In this position, the bone plate holder apparatus 101 can be inserted and removed by hand from the bone plate 102. FIG. 4B shows a similar partial side cutaway schematic view of an alternative embodiment employing grooves 111 in the prong working surfaces 110a, 110b for retaining the bone plate 102.

Figure 5:
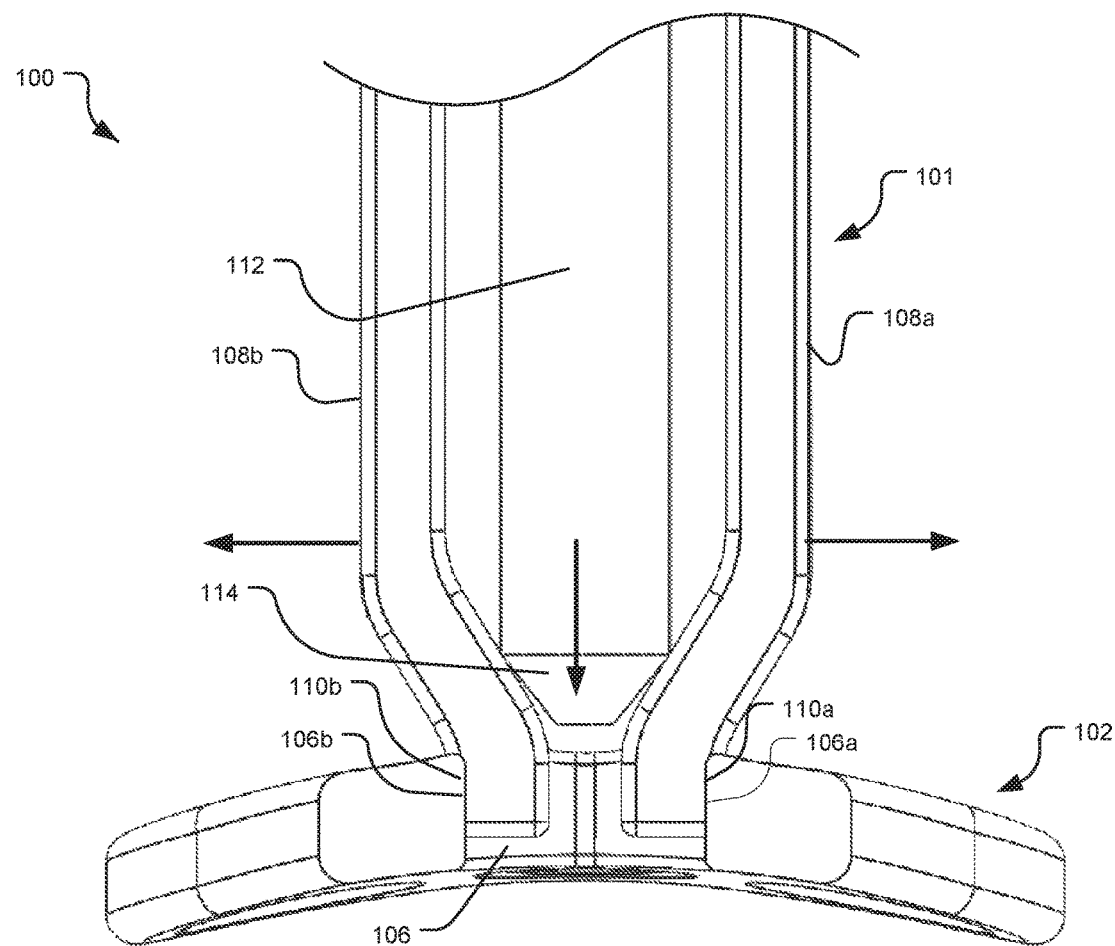
FIG. 5 is a partial side cutaway view of the plate holder system of FIG. 1, showing the working end of a plate holder apparatus interacting with a bone plate, in a locked position.

FIG. 5 is a partial side cutaway view of the bone plate holder system 100 of FIG. 1, showing the working end of bone plate holder apparatus 101 interacting with a bone plate 102, in the locked position. As shown in FIG. 5, the rod 112 is in a depressed position toward the bone plate 102 (compared to the unlocked position as shown in FIGS. 4A, 4B), such that the rod end 114 impinges on the prongs 108a, 108b, forcing them outward so that the prong working surfaces 110a, 110b of the prongs forcibly abut the interior faces 106a, 106b of the bone plate 102. In this position, the bone plate holder apparatus 101 is rigidly connected with the bone plate 102.

Figure 6:
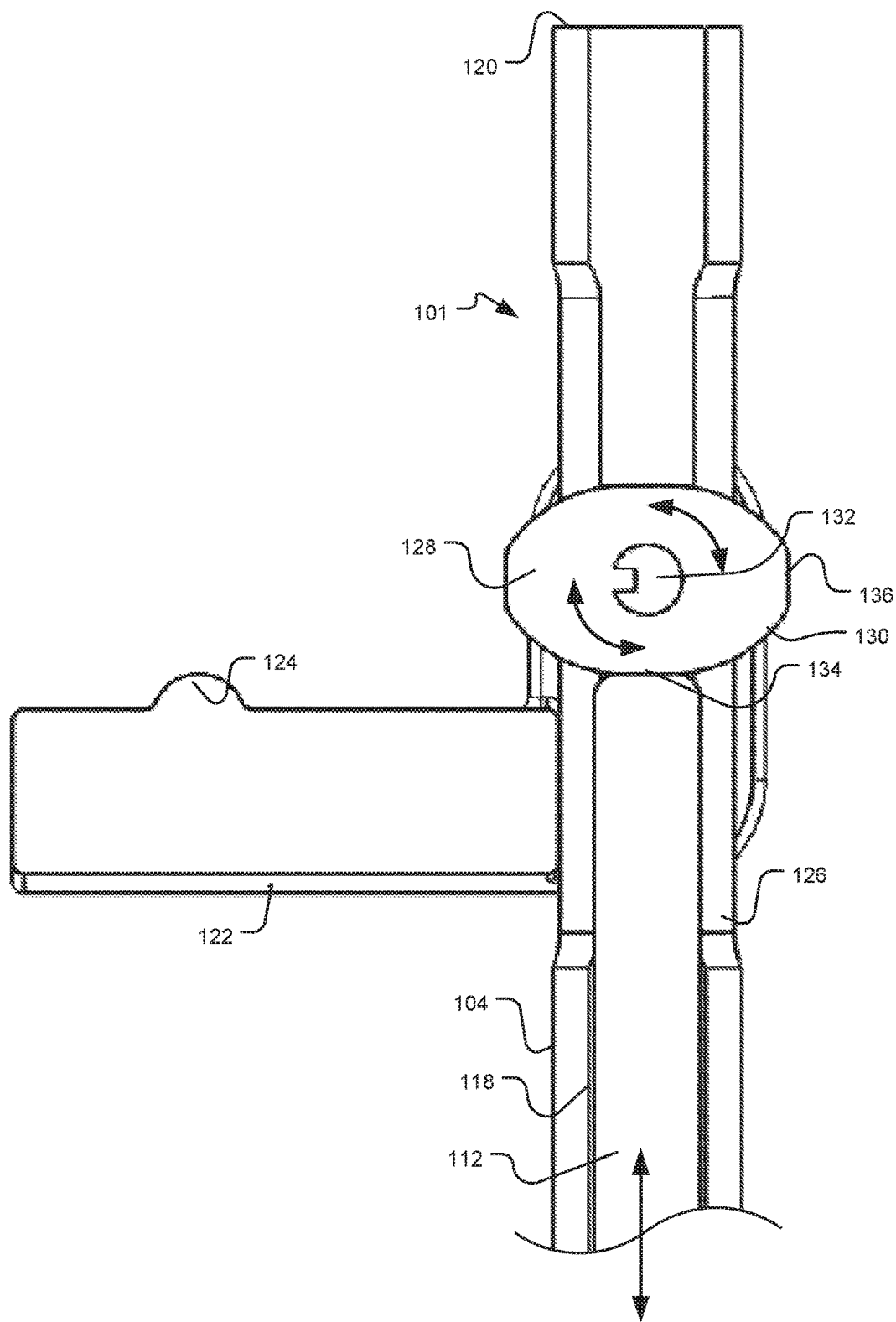
FIG. 6 is a partial side cutaway view of the plate holder apparatus of FIG. 1, showing the handle end in an unlocked position.

FIG. 6 is a partial side cutaway view of the bone plate holder apparatus 101 shown in FIG. 1, focusing on the handle end 120 in an unlocked position. The hollow elongate shaft 104 contains the rod 112 within the interior lumen 118 of the shaft, and the rod 112 is slidably disposed therein. The cam 128 is attached by an axle 132 through the hollow shaft 104, and attached with the handle 122 via the axle 132, so that the cam 128 can be rotated by manipulation of the handle 122. As shown, the cam 128 is positioned with a first flat surface 134 associated with a small radius within the lumen 118 of the shaft 104, such that the rod 112 abuts the first flat surface 134 and rests in a released or "unlocked" position. When the bone plate holder apparatus 101 is in the unlocked position, the second flat surface 136 associated with a large radius is positioned outside the lumen 118, through a cavity 126 in the hollow shaft 104. The curved cam working surface 130 falls between the first and second flat surfaces 134, 136 associated with the small and large radii of the cam 128. A positive surface feature 124 on the handle 122 controls a range of rotation of the handle 122.

Figure 7:
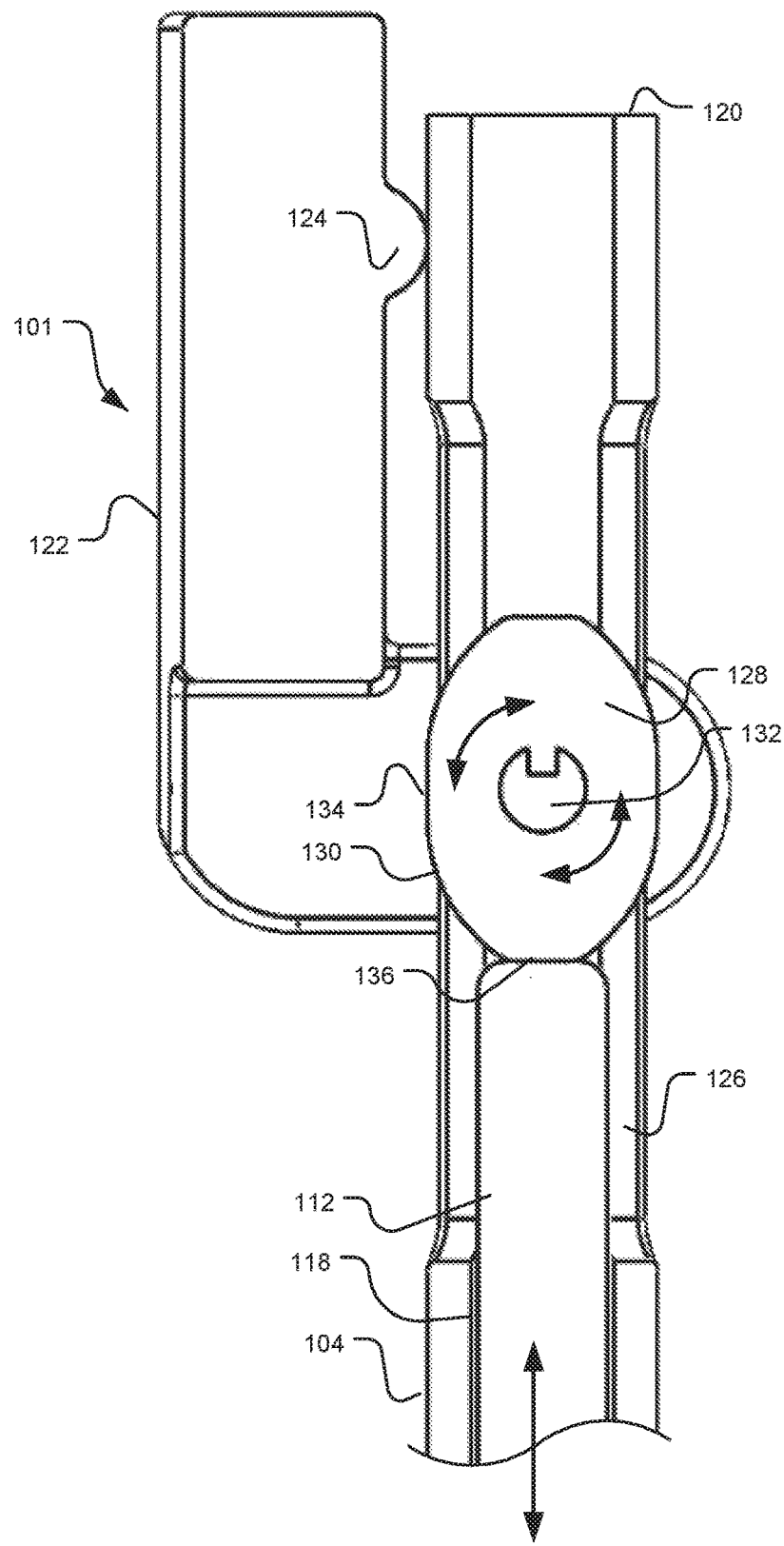
FIG. 7 is a partial side cutaway view of the plate older apparatus of FIG. 1, showing the handle end in a locked position.

FIG. 7 is a partial side cutaway view of the bone plate holder apparatus 101 shown in FIG. 1, focusing on the handle end 120 in a locked position. The hollow elongate shaft 104 contains the rod 112 within the interior lumen 118 of the shaft, and the rod 112 is slidably disposed therein. When the handle 122 is rotated toward the handle end 120 of the shaft 104, the cam 128 is caused to rotate with the handle 122 through approximately 90 degrees, until the handle 122 abuts the hollow shaft (via the surface feature 124). As the cam 128 rotates, the rod 112 is depressed by the curved working surface 130 of the cam 128, until the rod 112 comes to rest abutting the second flat surface 136 associated with the large radius of the cam 128, in a depressed or "locked" position.

Any other suitable mechanism may cause two or more prongs, such as the prongs 110a and 110 of FIGS. 1-5, to expand and revert according to the locked and unlocked positions, respectively. For example, a cam-driven system, like the system 100 as shown in FIGS. 1, 6 and 7, may possess a knob or dial coaxial to the cam, rather than a handle, for turning the cam between a locked and unlocked position. Alternatively, a different form or structure of a cam-driven device may be used. For example, rather than having a cam perpendicular to the shaft of a bone plate holder apparatus, said apparatus may include an in-line rotary cam pair for alternatingly supporting a rod at a depressed position and a released position. In the in-line rotary cam pair, upper and lower cams are coaxial with the shaft of the bone plate holder apparatus. When the upper cam is pressed for a first time onto a lower cam, the lower cam is depressed below an interior surface feature in the shaft lumen of the bone plate holder apparatus, whereupon the lower cam partially rotates so that its return path becomes blocked by the interior surface feature in the shaft lumen. When the upper cam is pressed a second time, the lower cam is again depressed below the level of the interior surface feature in the shaft lumen, whereupon the lower cam partially rotates a second time, so that its return path is no longer blocked by the interior surface feature. In such a configuration, a user would be able to lock and unlock the bone plate holder apparatus from a bone plate by repeatedly depressing a driving rod or switch connected with the upper cam. Further non-limiting examples of potentially suitable mechanisms of depressing a rod in a shaft of a bone plate holder apparatus may include a screw mechanism, a spring-loaded plunger, or a ratcheting mechanism with a release, or other mechanisms.

Figure 8:
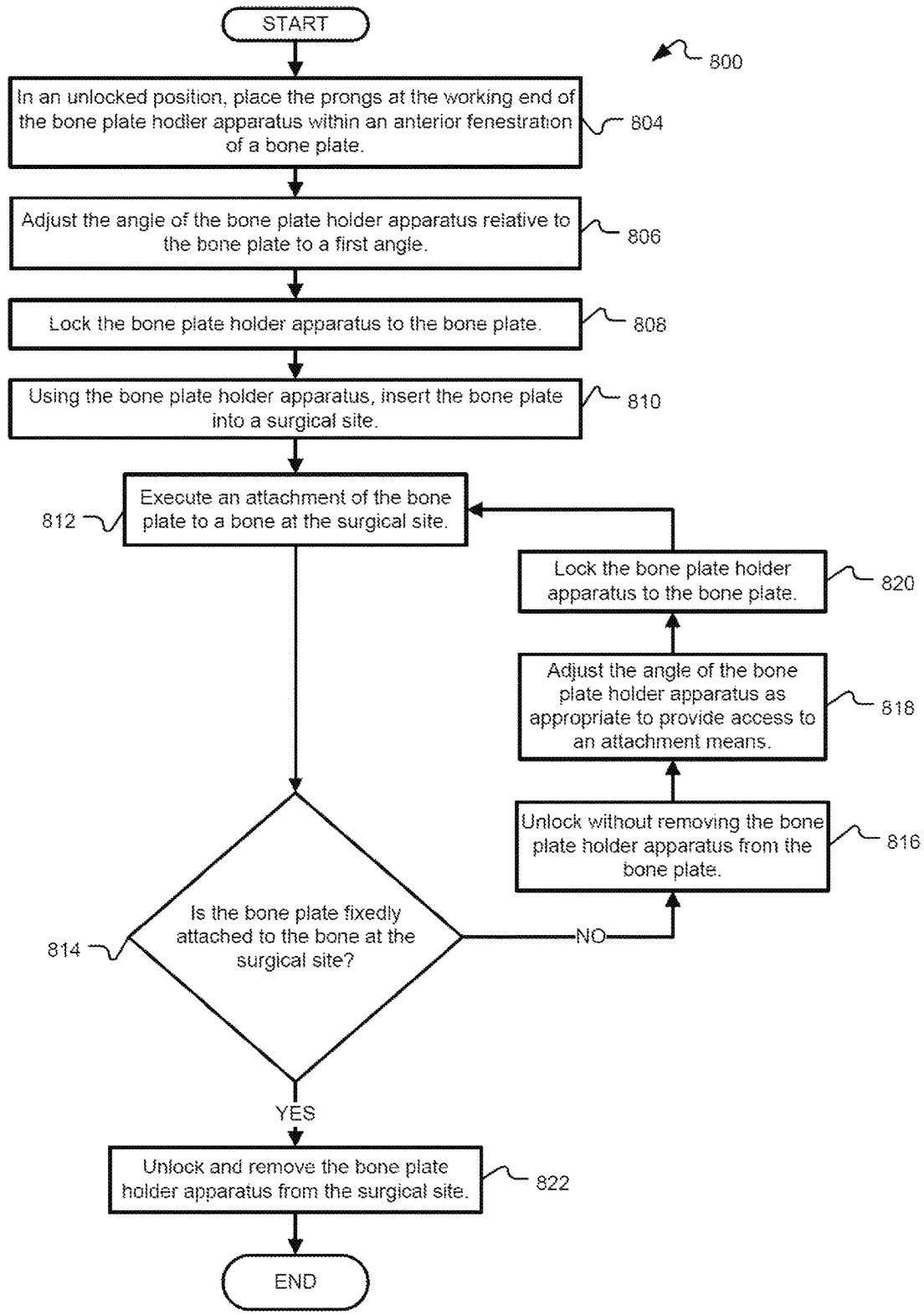
FIG. 8 is a process flow diagram illustrating an exemplary method for using a bone plate system.

FIG. 8 shows a non-limiting exemplary process 800 for using a bone plate system. In a surgical procedure, which may be an insertion of an anterior spinal bone plate, prongs at a working end of a bone plate holder apparatus (such as the bone plate holder apparatus 101 shown in FIGS. 1-7) may be inserted into an anterior fenestration in a bone plate (such as the fenestration 106 in the bone plate 102 shown in FIGS. 1-5) at step 804. A physician may, prior to locking the bone plate, manually adjust an angle of the bone plate holder apparatus to a first angle, which is chosen to permit access to the bone plate at a desired position (step 806). The bone plate holder apparatus is then locked to the bone plate, so as to prevent inadvertent release or change in angle (step 808). The physician then uses the bone plate holder apparatus to insert the bone plate into a surgical site (step 810), and executes an attachment procedure for fixedly attaching the bone plate to the bone at the surgical site (step 812). Attachment procedures may include, for example, attaching the bone plate to the bone by one or more bone screws. If the bone plate is not yet fully secured to the bone (step 814), the physician may unlock the bone plate holder apparatus from the bone plate without fully removing the holder apparatus (step 816), and may adjust the angle of the bone plate holder apparatus relative to the bone plate (step 818). When a desired second angle is achieved, the physician may then lock the bone plate holder apparatus to the bone plate (step 822) and continue to attach the bone plate to the bone. The angle of attachment between the bone plate holder apparatus and the bone plate may be adjusted repeatedly as needed. When the bone plate is fixedly attached with the surgical site, the physician unlocks and fully removes the bone plate holder apparatus from the bone plate (step 822).

In some cases, a bone plate system is designed such that a bone plate holder apparatus, such as bone plate holder apparatus 101, can be fixed to a bone plate, such as bone plate 102, while still allowing transverse movement of the bone plate holder apparatus relative to the bone plate. This feature gives the physician flexibility to adjust the attachment point between the bone plate holder apparatus and the bone plate without having to disengage the apparatus from the bone plate during a critical moment of the procedure. As one non-limiting example, a physician may optionally reposition a bone plate holder apparatus along a fenestration in a bone plate during a surgical procedure. For example, in the bone plate holder system 100 shown in FIG. 1, the bone plate holder apparatus 101 is shown interacting with a fenestration 106 in bone plate 102. The physician may attach and lock the bone plate holder apparatus at a first attachment location within the fenestration 106, the first attachment location being independent from an angle of attachment. Instead of or in addition to adjusting the angle, a physician may also adjust the position within the fenestration 106. This adjustment may be particularly useful or visible with bone plates having a substantially elongate fenestration, or bone plates having more than one fenestration interrupted by features not present in bone plate 102 shown in FIG. 1. For example, bone plates having features for attachment to three or more individual vertebrae may possess fenestrations separated by those features for attachment, and the same or multiple bone plate holder apparatuses may be attached to each of the fenestrations. In some cases, the bone plate holder apparatus may be moved along a path defined by the fenestration. In a subset of said cases, the bone plate holder apparatus may be partially or fully unlocked prior to being moved along said path. In an alternate subset, the attachment between the bone plate holder apparatus and the bone plate may be sufficiently loose that a practitioner can adjust the exact positioning by the application of force.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate examples of the invention and does not pose a limitation on the scope of the invention unless otherwise claimed. No language in the specification should be construed as indicating any non-claimed element as essential to the practice of the invention.

Various embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A bone plate holder apparatus comprising:
    a substantially elongate shaft comprising a working end and a handle end;
    a pair of opposed prongs at the working end of the substantially elongate shaft, the pair of opposed prongs converging toward a longitudinal axis of the substantially elongate shaft and comprising a pair of outwardly facing surfaces configured to mate with an elongate interior fenestration in a bone plate;
    an elongate rod disposed substantially parallel to the substantially elongate shaft, the elongate rod being configured to interfere with the pair of opposed prongs at a first end of the elongate rod and press the pair of opposed prongs outward away from each other into a locked position when the elongate rod is pressed toward the working end; and a locking mechanism having a first position and a second position, the first position being associated with an unlocked position of the elongate rod where the elongate rod does not interfere with the pair of opposed prongs, and the second position being associated with the locked position of the elongate rod where the elongate rod interferes with the pair of opposed prongs, and wherein the locking mechanism causes the elongate rod to be pressed from the unlocked position to the locked position, and wherein the pair of opposed prongs is shaped such that, when the pair of opposed prongs is fully inserted in the elongate interior fenestration of the bone plate and the locking mechanism is in the second position, the pair of opposed prongs interfere with the elongate interior fenestration to retain the bone plate and the bone plate holder can be angularly adjusted relative to the bone plate.

2. The bone plate holder apparatus of claim 1, wherein the substantially elongate shaft is hollow, and wherein the elongate rod is disposed coaxially inside the hollow substantially elongate shaft.

3. The bone plate holder apparatus of claim 2, wherein the hollow substantially elongate shaft further comprises one or more fenestrations in a wall of the hollow substantially elongate shaft to provide access to an interior of the shaft.

4. The bone plate holder apparatus of claim 1, wherein the substantially elongate shaft further comprises a knurled or textured surface feature that provides a gripping surface.

5. The bone plate holder apparatus of claim 1, further comprising:
one or more first surface features within a lumen of the substantially elongate shaft configured to stop a motion of the elongate rod within the substantially elongate shaft at one or more of a minimum travel and a maximum travel of the elongate rod relative to the substantially elongate shaft.

6. The bone plate holder apparatus of claim 1, wherein the locking mechanism comprises:
a cam having an axis of rotation perpendicular to the longitudinal axis of the substantially elongate shaft and disposed proximate to the handle end, the cam being positioned such that a working surface at an outside edge of the cam abuts a second end of the elongate rod, and the cam comprising a variable radius such that the working surface of the cam can alternatingly press and release the elongate rod; and
a rotating mechanism attached with the cam, the rotating mechanism configured to cause the cam to rotate between the first position and the second position.

7. The bone plate holder apparatus of claim 6, wherein the working surface of the cam comprises at least a first flat portion, a second flat portion, and a curved portion between the first and second flat portions, the first flat portion corresponding to the unlocked position and the second flat portion corresponding to the locked position, such that the cam may occupy a first stable position when in the unlocked position and may occupy a second stable position when in the locked position.

8. The bone plate holder apparatus of claim 6, wherein the rotating mechanism comprises a handle.

9. The bone plate holder apparatus of claim 8, wherein the handle comprises one or more surface features positioned to interact with the substantially elongate shaft such that the one or more surface features limit a range of angles of the handle relative to the substantially elongate shaft when the handle moves between the unlocked position and the locked position.

10. The bone plate holder apparatus of claim 1, wherein the locking mechanism is controlled to rotate through a range of approximately 90 degrees between the locked position and the unlocked position.

11. The bone plate holder apparatus of claim 1, wherein:
each prong of the pair of opposed prongs further comprises a prong working surface; and
each prong working surface further comprises a groove shaped to interact with the bone plate.

12. The bone plate holder apparatus of claim 11, wherein each prong working surface further comprises a plurality of grooves angled relative to the bone plate holder apparatus to provide for a plurality of holding angles of the bone plate.

13. The bone plate holder apparatus of claim 1, wherein:
each prong of the pair of opposed prongs further comprises a prong working surface; and
each prong working surface further comprises one or more grip enhancing features.

14. The bone plate holder apparatus of claim 1, wherein the pair of opposed prongs are configured to press against the elongate rod when the elongate rod is pressed toward the working end, such that the pair of opposed prongs tend to push the elongate rod toward the unlocked position when the elongate rod is in the locked position.

15. The bone plate holder apparatus of claim 1, further comprising a spring assembly interior to the substantially elongate shaft, the spring assembly configured to interact with the elongate rod so as to press the elongate rod toward the unlocked position such that, when the locking mechanism is in the first position, the elongate rod is retained in the unlocked position by the spring assembly.

16. The bone plate holder apparatus of claim 1, wherein each prong of the pair of opposed prongs comprises a respective substantially flat working surface configured to interface with a respective substantially flat portion of an interior side of an elongate interior fenestration of a medical implant.

17. The bone plate holder of claim 1, wherein the first and second positions of the locking mechanism correspond to a minimum and maximum travel of the elongate rod, respectively.

18. The bone plate holder of claim 1, wherein the pair of opposed prongs are pivotable within the elongate fenestration when attached to the bone plate while retaining the bone plate.

19. A bone plate holder system comprising:
(1) a bone plate holder apparatus comprising:
a substantially elongate shaft comprising a working end and a handle end;
pair of opposed prongs attached with the substantially elongate shaft at the working end, the pair of opposed prongs converging toward a longitudinal axis of the substantially elongate shaft;
an elongate rod disposed substantially parallel to the substantially elongate shaft, the elongate rod being configured to interfere with the pair of opposed prongs at a first end of the elongate rod and press the pair of opposed prongs outward away from each other into a locked position when the elongate rod is pressed toward the working end; and
a locking mechanism having a first position and a second position, the first position being associated with an unlocked position of the elongate rod where the elongate rod does not interfere with the pair of opposed prongs, and the second position being associated with the locked position of the elongate rod where the elongate rod interferes with the pair of opposed prongs, and wherein the locking mechanism causes the elongate rod to be pressed from the unlocked position to the locked position; and (2) a bone plate having an elongate interior fenestration sized to accommodate the pair of opposed prongs, such that the pair of opposed prongs interfere with the elongate interior fenestration when the locking mechanism is in the second position, wherein the pair of opposed prongs is shaped such that, when the pair of opposed prongs is inserted in the elongate interior fenestration of the bone plate and the locking mechanism is in the second position, the bone plate holder apparatus can be angularly adjusted relative to the bone plate.

20. The system of claim 19, wherein:
when the locking mechanism is in the first position, the bone plate holder apparatus can be inserted into, removed from, or adjusted in angle relative to the fenestration of the bone plate.

\* \* \* \* \*